US012558233B2

(12) United States Patent
Harris et al.

(10) Patent No.: US 12,558,233 B2
(45) Date of Patent: *Feb. 24, 2026

(54) APPARATUS AND METHOD FOR REMOVAL OF ACETABULAR CUP WITH MINIMAL BONE LOSS

(71) Applicants: Adam Harris, San Antonio, TX (US); Evan Harris, San Antonio, TX (US)

(72) Inventors: Adam Harris, San Antonio, TX (US); Evan Harris, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/735,403

(22) Filed: Jun. 6, 2024

(65) Prior Publication Data

US 2024/0315854 A1 Sep. 26, 2024

Related U.S. Application Data

(63) Continuation of application No. 17/578,736, filed on Jan. 19, 2022, now Pat. No. 12,029,661.

(51) Int. Cl.
*A61F 2/46* (2006.01)
*A61B 17/16* (2006.01)
*A61F 2/30* (2006.01)

(52) U.S. Cl.
CPC ........ *A61F 2/4609* (2013.01); *A61B 17/1666* (2013.01); *A61F 2002/3069* (2013.01); *A61F 2002/4619* (2013.01)

(58) Field of Classification Search
CPC ........... A61F 2/4609; A61F 2002/4619; A61B 17/1666
See application file for complete search history.

(56) References Cited

U.S. PATENT DOCUMENTS

| | | | |
|---|---|---|---|
| 5,941,899 A * | 8/1999 | Granger | A61B 17/06066 606/222 |
| 7,763,031 B2 * | 7/2010 | Tulkis | A61B 17/1666 606/81 |
| 10,342,553 B2 | 7/2019 | Gilhooley | |
| 11,147,689 B2 * | 10/2021 | Nic | A61B 17/142 |
| 11,253,375 B2 * | 2/2022 | Siccardi | A61F 2/4609 |
| 11,504,250 B2 * | 11/2022 | Sweitzer | A61F 2/4609 |

(Continued)

FOREIGN PATENT DOCUMENTS

| | | | | |
|---|---|---|---|---|
| EP | 3431046 A1 * | 1/2019 | | A61F 2/4609 |
| WO | WO-0069347 A1 * | 11/2000 | | A61B 17/1604 |

*Primary Examiner* — Anu Ramana
(74) *Attorney, Agent, or Firm* — Maier & Maier, PLLC

(57) ABSTRACT

An acetabular cup removal device and method. The removal device can include a mounting ring attachable to an acetabular cup, a rotor rotatably coupled to the mounting ring and rotatable about a first axis, an arm pivotably coupled to the rotor and pivotable about a second axis orthogonal to the first axis, an oscillator assembly slidably disposed in a first slit of the arm, and a blade slidably disposed in a second slit of the arm. A rotation of the oscillator assembly causes an oscillation of the blade within the second slit. The removal method includes coupling the device to an acetabular cup, positioning the arm and blade at an initial location, oscillating the blade so as to perform a cut, repositioning the arm at a subsequent adjacent location, repeating the repositioning and oscillating steps until a 360° circumference is cut around the acetabular cup, and removing the acetabular cup.

5 Claims, 7 Drawing Sheets

(56)         References Cited

U.S. PATENT DOCUMENTS

| | | | |
|---|---|---|---|
| 2002/0116007 A1* | 8/2002 | Lewis .................. | A61F 2/4609 |
| | | | 606/99 |
| 2003/0176867 A1* | 9/2003 | Long ................... | A61B 17/142 |
| | | | 606/79 |
| 2008/0294169 A1 | 11/2008 | Scott | |
| 2010/0228259 A1* | 9/2010 | Tulkis ................. | A61F 2/4609 |
| | | | 606/99 |
| 2015/0359641 A1* | 12/2015 | Nic ................... | A61B 17/1637 |
| | | | 606/81 |
| 2016/0206326 A1* | 7/2016 | Gilhooley .......... | A61B 17/1637 |
| 2019/0021879 A1* | 1/2019 | Sweitzer .............. | A61F 2/4609 |

* cited by examiner

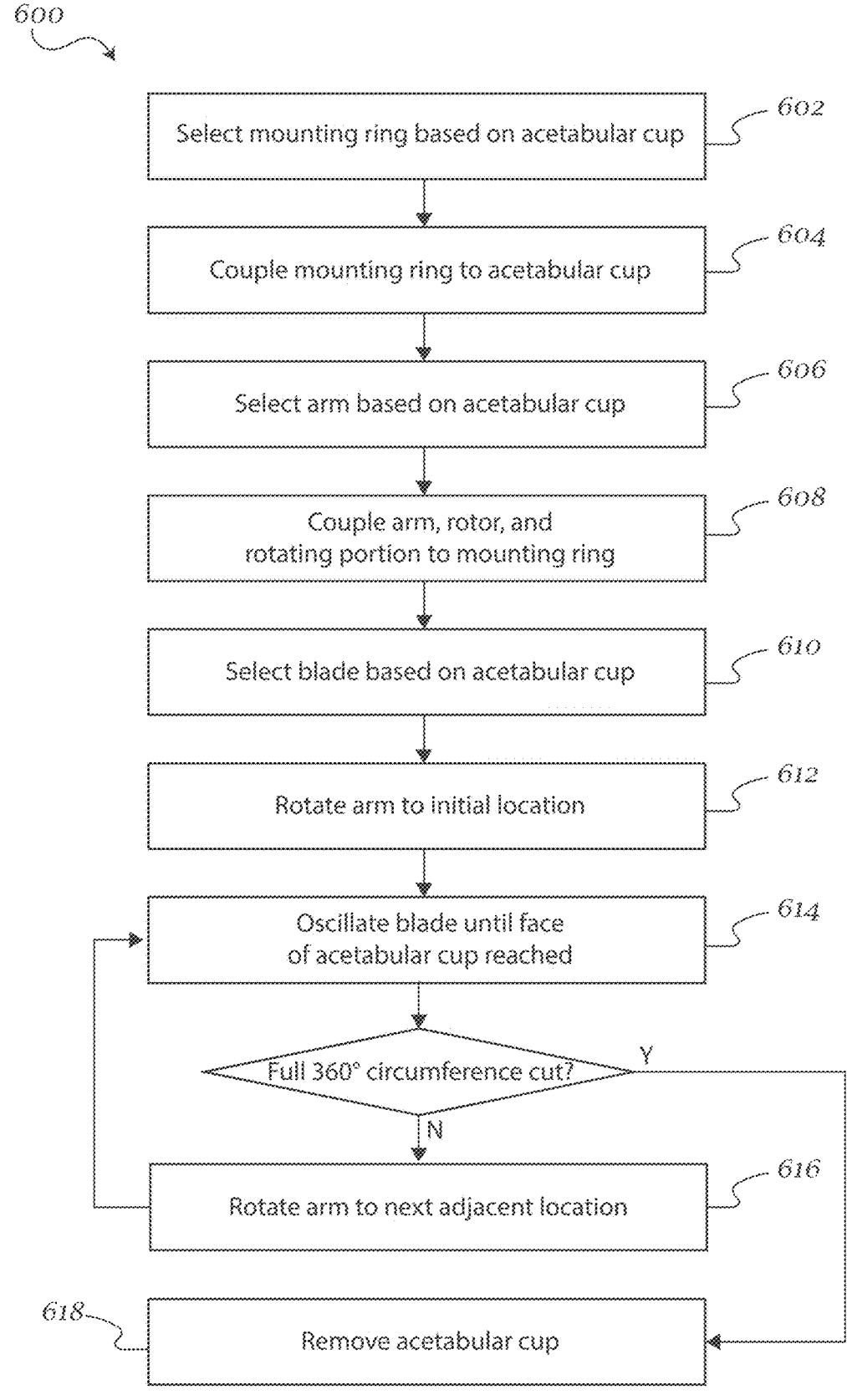

*600*

Select mounting ring based on acetabular cup — *602*

Couple mounting ring to acetabular cup — *604*

Select arm based on acetabular cup — *606*

Couple arm, rotor, and
rotating portion to mounting ring — *608*

Select blade based on acetabular cup — *610*

Rotate arm to initial location — *612*

Oscillate blade until face
of acetabular cup reached — *614*

Full 360° circumference cut? — Y — N

Rotate arm to next adjacent location — *616*

*618* — Remove acetabular cup

*Fig. 7*

APPARATUS AND METHOD FOR REMOVAL OF ACETABULAR CUP WITH MINIMAL BONE LOSS

CROSS-REFERENCE TO RELATED APPLICATIONS

This application is a Continuation of U.S. application Ser. No. 17/578,736, filed on Jan. 19, 2022, which has issued as U.S. Pat. No. 12,029,661, the entire contents of which are incorporated herein by reference.

BACKGROUND

Multiple clinical indications exist for revision hip replacement. A surgical plan for revision hip replacement often includes the removal of a previously-placed acetabular component. Acetabular components are generally hemispherical in shape, and can vary in diameter. A goal of the revision hip replacement surgery is to remove the acetabular component with minimal loss of bone. Doing so can be challenging, in particular if the acetabular component is or has become poorly positioned.

Osteotomes are the typical instruments for removing an acetabular component, and several types of these are known. The first type includes sets of curved and offset osteotomes. Such osteotomes work well if there exists an adequate exposure and a proper orientation of the cup. The second type adds a centering ball and a variety of blades having differing radii and lengths to the curved osteotome. The centering ball allows for easier proper placement of the osteotome, and diminishes bone loss associated with acetabular removal. However, both of these systems have difficulty with the initial placement of the osteotome, particularly the if the osteotome is long enough to cover 90 degrees of arc. Both types of osteotomes also do not interact well with acetabular cup designs that have spikes either at the rim, or deeper on the backside of the cup.

More recently, powered versions that make use of either curved or circular saw blades, rather than osteotomes, have been introduced. While such designs can be considered an improvement, their applications can be limited. Such currently available devices require direct, perpendicular access to the acetabular component. This can be a significant issue when the acetabular cup is malpositioned, or when the surgical exposure is limited for any reason. In such cases, access to the acetabular cup would require significant dissection of the surrounding tissues, or may be altogether impossible. Such designs are also limited in their efficacy in cases where there are non-spherical aspects of the acetabular cup's design.

An improved device that addresses the above issues is therefore desired.

SUMMARY

According to at least one exemplary embodiment, an acetabular cup removal device is disclosed. The acetabular cup removal device can include a mounting ring attachable to an acetabular cup, a rotor rotatably coupled to the mounting ring and rotatable about a first axis, an arm pivotably coupled to the rotor and pivotable about a second axis orthogonal to the first axis, the arm having a first slit and a second slit, an oscillator assembly slidably disposed in the first slit, a blade slidably disposed in the second slit. A rotating motion of a rotating portion of the oscillator assembly causes an oscillating motion of the blade within the second slit.

According to a further exemplary embodiment, the mounting ring can include a ring portion coupled to a central hub, a mounting member coupled to the central hub and offset from the central hub, a first bore defined in the central hub, and a second bore defined in the mounting member. The first bore and the second bore can be collinear with the first axis.

According to a further exemplary embodiment, the arm can include an elongated portion in which the first slit is defined, the elongated portion having a distal end and a proximal end coupled to the rotor, and a curved portion in which the second slit is defined, the curved portion extending from the distal end of the elongated portion. A first end of the elongated portion can be disposed at the distal end of the elongated portion, and a second end of the curved portion can be closer than the first end, along a length of the elongated portion, to the proximal end of the elongated portion.

According to a further exemplary embodiment, the oscillator assembly can include a sliding portion having a main block, a tab extending from a first surface of the main block and slidably disposed in the first slit, and a groove defined in a second surface of the main block that is opposite a first surface, a first pin extending from the second surface, a rotating portion rotatably mounted on the first pin and having a face gear defined on a groove-facing surface, and a second pin extending from a surface of the rotating portion that is opposite the groove-facing surface.

According to another exemplary embodiment, a method for removing an acetabular cup can include the steps of coupling an acetabular cup removal device to an acetabular cup of a patient, positioning an arm having a blade slidably coupled thereto at an initial location, oscillating the blade so as to perform a cut, repositioning the arm at a subsequent location adjacent a location that was cut prior to the subsequent location, repeating the oscillating and repositioning steps until a 360° circumference is cut around the acetabular cup and removing the acetabular cup from the patient.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 7 shows an exemplary method for removing an acetabular cup.

DETAILED DESCRIPTION

Aspects of the invention are disclosed in the following description and related drawings directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1A:
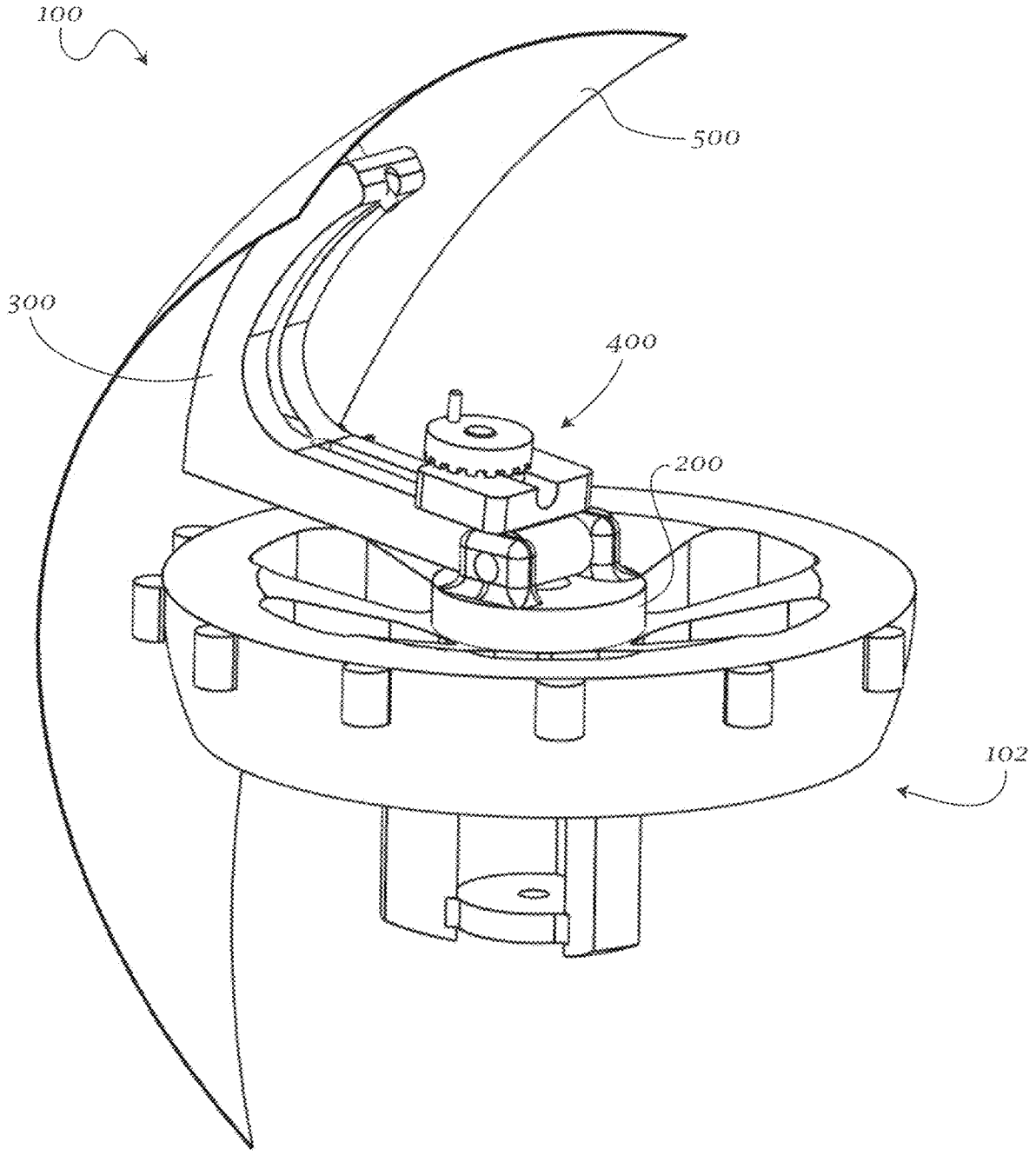
FIG. 1A shows an exemplary embodiment of an acetabular cup removal device.
Figure 1B:
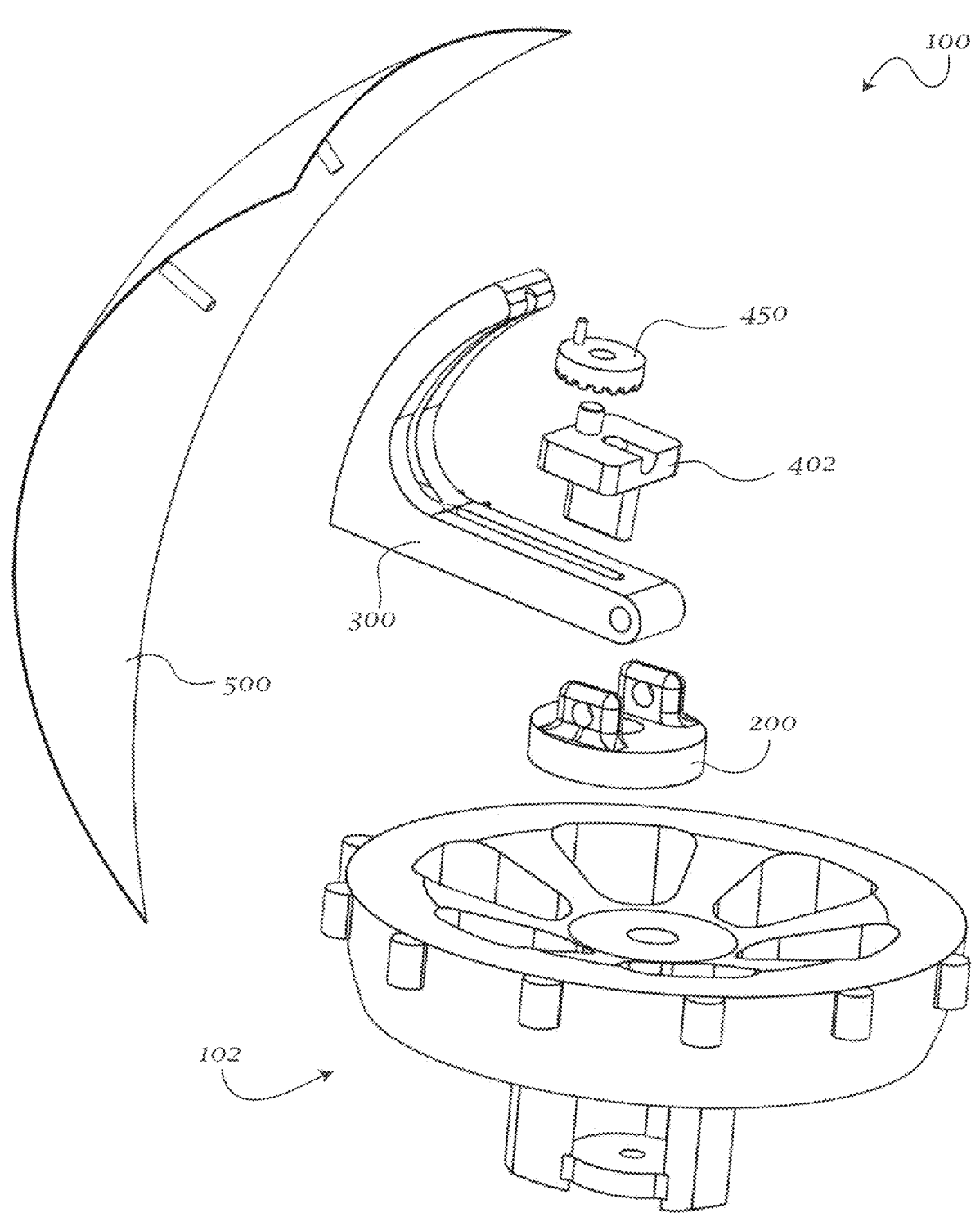
FIG. 1B is an exploded view of an exemplary embodiment of an acetabular cup removal device.

According to at least one exemplary embodiment, and as shown in FIGS. 1A-1B, an acetabular cup removal device 100 is disclosed. The cup removal device 100 is configured to couple to an acetabular cup and to cut away the acetabular cup from the surrounding bone so that it may be excised from the patient with minimal bone loss. The acetabular cup removal device 100 can include a mounting ring 102, a rotor 200, an arm 300, an oscillator assembly 400, and a blade 500.

Figure 2A:
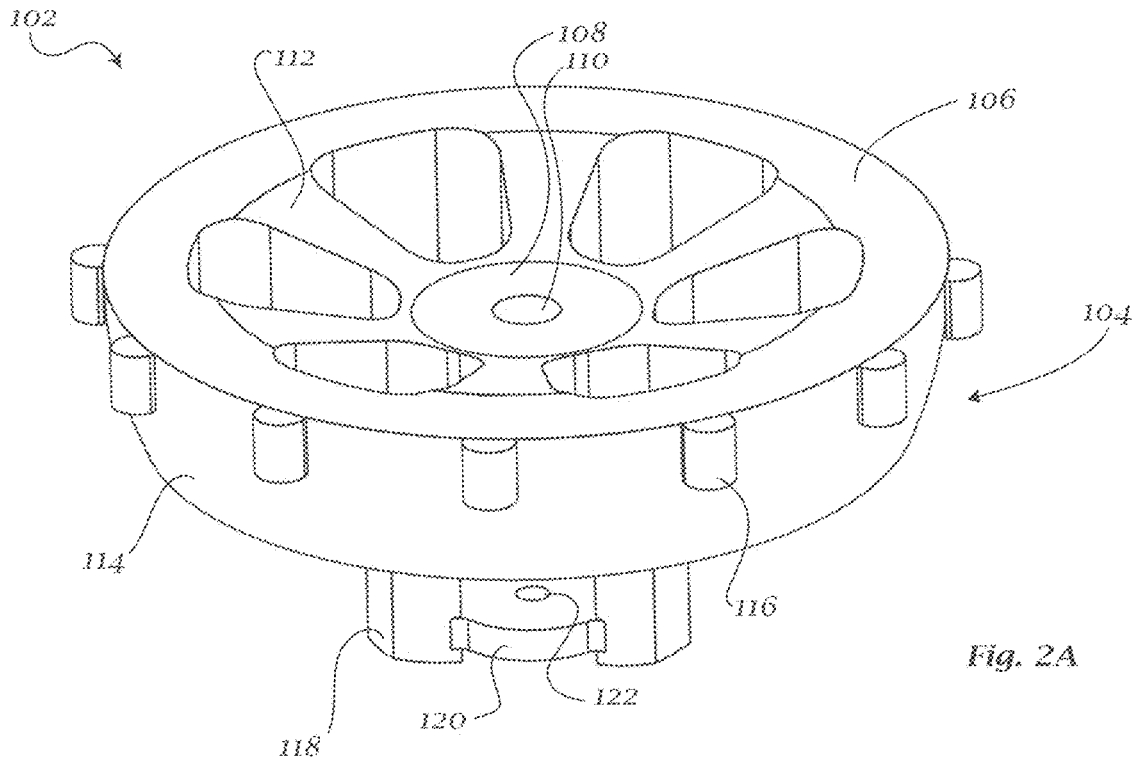
FIG. 2A shows an exemplary mounting ring of an acetabular cup removal device.
Figure 2B:
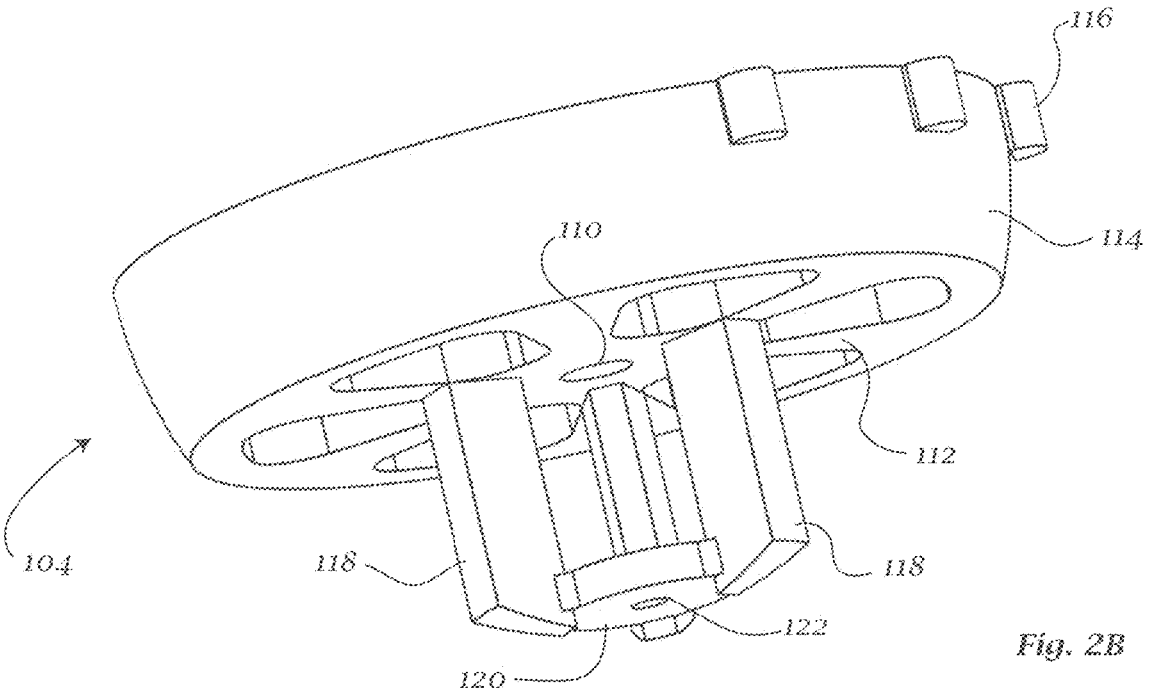
FIG. 2B shows an exemplary mounting ring of an acetabular cup removal device.

As shown in FIGS. 2A-2B, the mounting ring 102 may have a ring portion 104 which may have a cylindrical or partially-hemispherical shape. An outer ring 106 of the ring portion 104 may be connected to a central hub 108 by a plurality of spokes 112. Central hub 108 may further be provided with a bore 110 extending vertically through the center thereof. Further, in some embodiments, the upper surface of central hub 108 may be vertically offset from the upper surface of outer ring 106 so as to be lower than the upper surface of the outer ring. Consequently, the upper surfaces of spokes 112 may be oriented in planes diagonal to those of the upper surfaces of the hub and the outer ring. In turn, the lower surface of ring portion 104, i.e., the lower surfaces of outer ring 106, central hub 108, and spokes 112, may all be disposed in the same plane, which may parallel to the plane of the upper surfaces of outer ring 106 and central hub 108. However, any configuration for ring portion 104 that enables device 100 to function as described herein may be contemplated and provided as desired.

Provided on the outer surface 114 of outer ring 104 may be a plurality of mounting pips 116. Mounting pips 116 may have a cylindrical or semi-cylindrical shape, and may be disposed along at least a portion of the circumference of outer ring 104. Mounting pips 116 may be adapted to engage a portion of the acetabular cup, such as, for example, matching recesses on the acetabular cup or a liner thereof (not shown). Alternatively, other structures may be provided for engagement with a portion of the acetabular cup; for example, a latching mechanism may be provided so as to engage with slots on an acetabular cup of a type such as a Birmingham hip. Therefore, the size, shape, number and shape of mounting pips, and other such features of outer ring 104 may be customized so as to engage a specific type, brand, and/or model of acetabular cup so as to enable device 100 to function as described herein. Further, the shape of surface 114 may be sized and shaped to match an inner surface of the acetabular cup that is being removed. Mounting pips 116 can facilitate ensuring a stable mounting of device 100 and to prevent rotation of device 100 with respect to the acetabular cup that is being removed.

Extending substantially vertically and downward from the lower surface of ring portion 104 may be a plurality of supports 118. Disposed between and substantially at the lower ends of supports 118 may be a mounting member 120, which is provided with a fastening bore 122 extending vertically therethrough, within which a fastener may be received. Fastening bore 122 can be provided on the central axis of mounting ring 102. The inner surface of fastening bore 122 may be threaded, so as to engage a threaded fastener.

Figure 3:
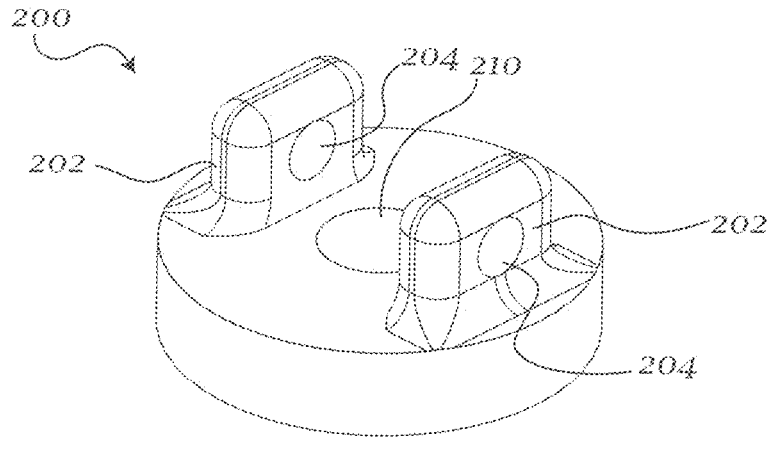
FIG. 3 shows an exemplary rotor of an acetabular cup removal device.

Turning to FIG. 3, rotor 200 can be rotatably coupled to the upper surface of central hub 108. Rotor 200 can have a cylindrical shape and can be provided with a bore 210 extending vertically through the center of rotor 200. A pin, bolt, or similar structure extending through bores 110, 210 can connect rotor 200 to mounting ring 102. Extending upwardly from the upper surface of rotor 200, and positioned opposite each other, may be a pair of tabs 202. Each of tabs 202 may be provided with a bore 204 extending horizontally therethrough, with both bores 202 being aligned with each other.

Figure 4:
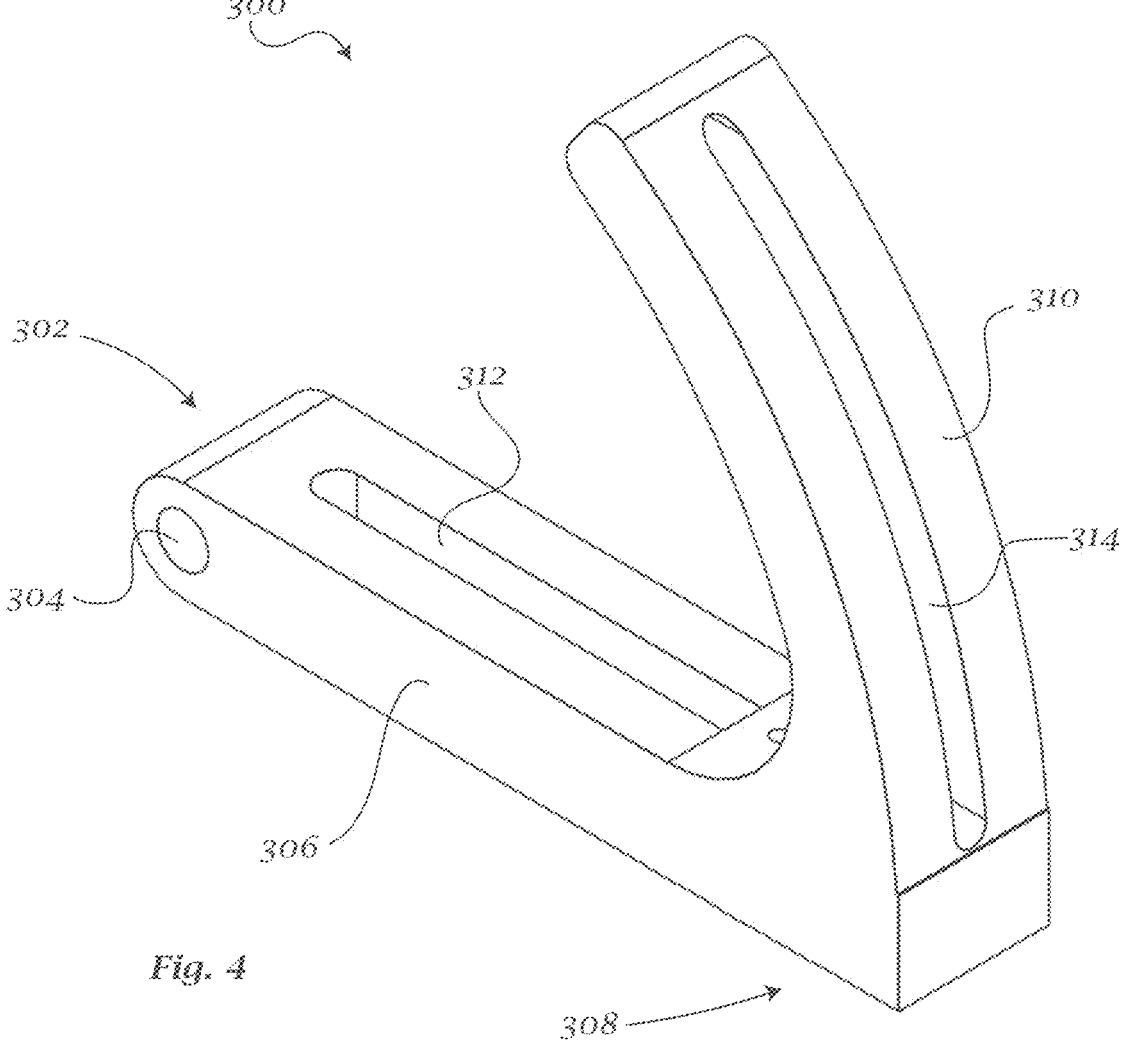
FIG. 4 shows an exemplary arm of an acetabular cup removal device.

Pivotably coupled to rotor 200 can be arm 300, shown in FIG. 4. A horizontal bore 304 can be provided at a proximal end 302 of arm 300, and can be aligned with bores 204 of the rotor. A pin, bolt, or similar structure extending through bores 204, 304 can connect arm 300 to rotor 300. Arm 300 can include an elongated portion 306 extending from proximal end 302, and a curved portion 310 extending upwardly from the distal end 308 of elongated portion 306 and curving inwardly in the direction of proximal end 302. A first slit 312 can be defined in elongated portion 306, and a second slit 314 can be defined in curved portion 310. Slits 312, 314 can extend along the centerlines and in the length directions of their corresponding portions. The lengths of slits 312, 314 may be adapted for the particular acetabular cup that device 100 is being used to remove. The radial length of arm 300 may be such that distal end 308 is located substantially over the outer diameter of the particular acetabular cup. Blade 500 can therefore be positioned at a radial position slightly greater than the outer diameter of the particular acetabular cup, so as to allow blade 500 to cut as close to the edge of the cup as possible, thereby minimizing the bone material that is removed.

Figure 5A:
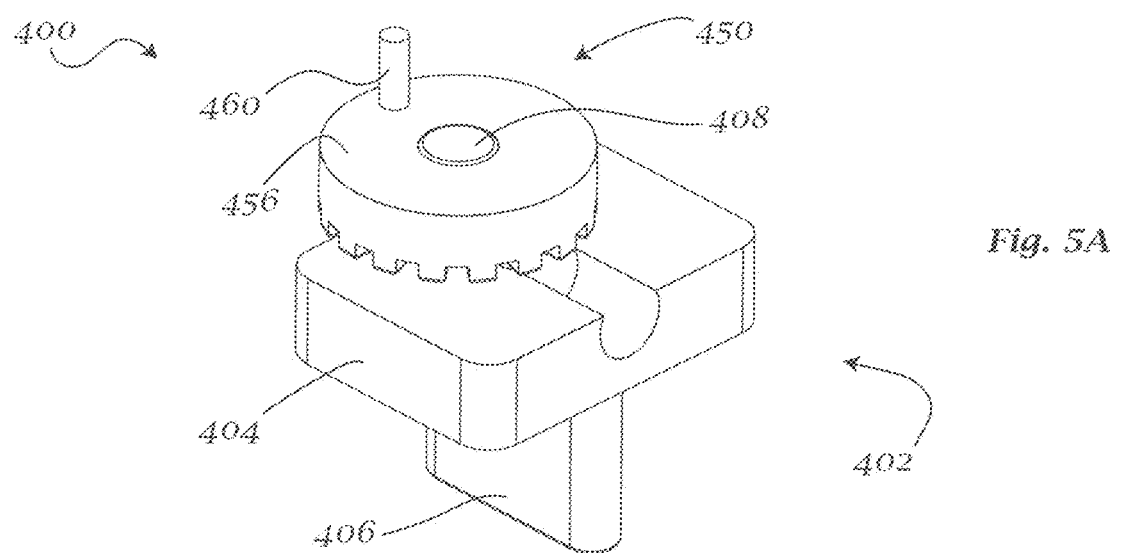
FIG. 5A shows an exemplary oscillator mechanism of an acetabular cup removal device.
Figure 5B:
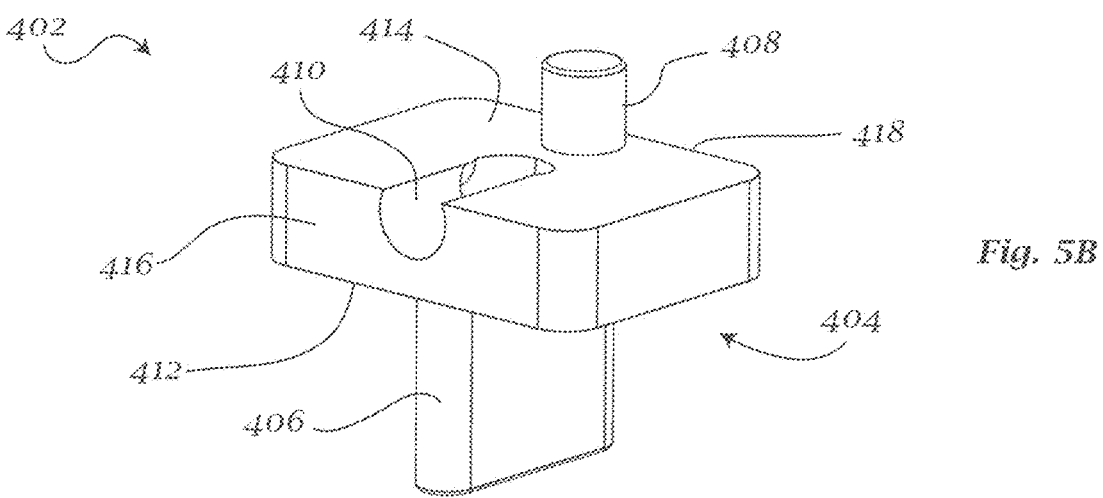
FIG. 5B shows an exemplary sliding portion of the oscillator mechanism.
Figure 5C:
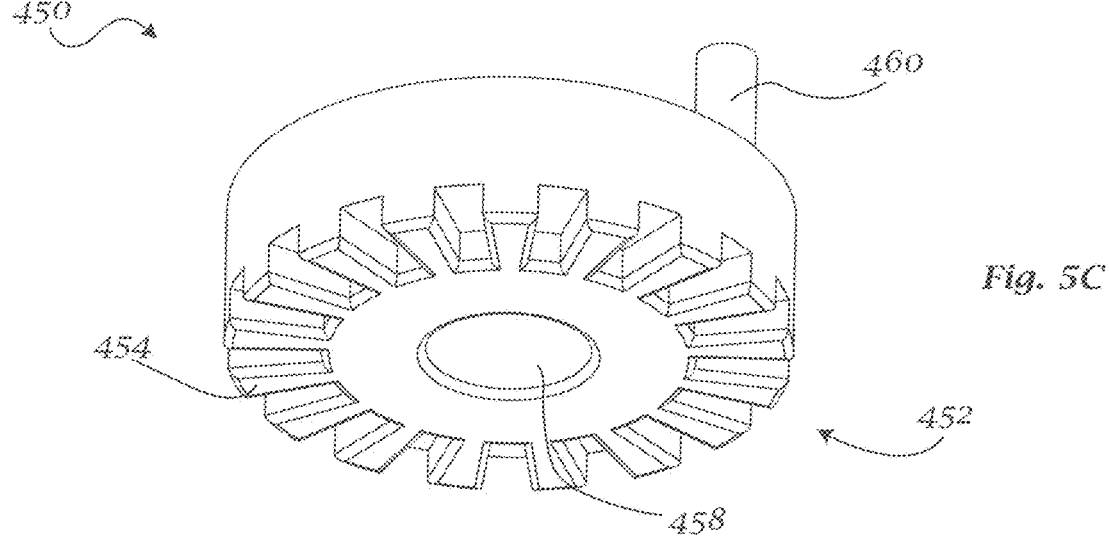
FIG. 5C shows an exemplary rotating portion of the oscillator mechanism.
Figure 6:
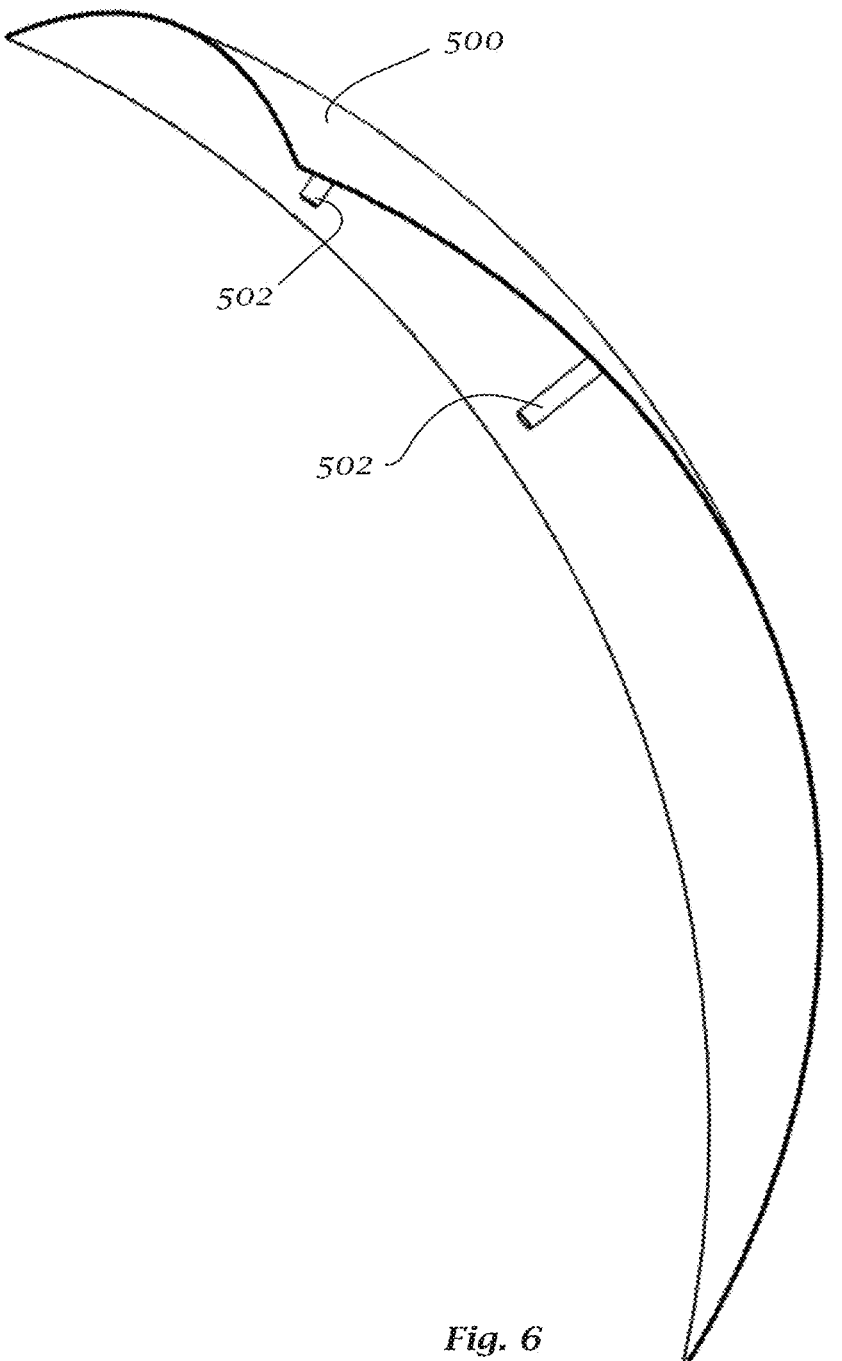
FIG. 6 shows an exemplary blade of an acetabular cup removal device.

Turning to FIGS. 5A-5C, oscillator assembly 400 can be slidably coupled to first slit 312 of arm 300. The oscillator assembly can include a sliding portion 402 and a rotating portion 450. Sliding portion 402 can include a main block 404, a tab 406 extending vertically downward from the lower surface 412 of main block 404, and a cylindrical pin 408 extending vertically upward from the upper surface 414 of main block 404. Main block 404 can have a substantially rectangular or round-rectangular prism shape, with the major axis of block 404 being perpendicular to the major axis of tab 406. Tab 406 can likewise have a substantially rectangular or round-rectangular prism shape and can further be sized and shaped to fit snugly yet slidably within first slit 312 of arm 300. An elongated groove 410 may be defined in the upper surface 414 of block 404, with the major axis of groove 404 being coplanar with the major axis of tab 406. Groove 410 may further have a partially circular cross-section. Groove 410 may have a first end disposed at a first longitudinal edge 416 of block 404 such that a cutout is defined in the edge, and a second end disposed substantially at the center of the block 404. Pin 408 may be disposed between the second end of groove 410 and a second longitudinal edge 418 of block 404.

Rotating portion 450 may have a cylindrical shape and may have a bore 458 extending vertically through the center thereof, bore 458 being sized and shaped to rotatably receive cylindrical pin 408 therein. The lower surface of rotating portion 450 may be designed as a face gear 452 having a plurality of gear teeth 454 extending radially towards the circumferential edge of rotating portion 450. The upper surface 456 of rotating portion 450 may have a cylindrical pin 460 positioned eccentrically thereon and extending vertically upward therefrom.

The oscillating mechanism may be powered externally. For example, rotary power may be provided via a rotating member (not shown), which may be, for example, a flexible rotating shaft. A head of the rotating member may be rotatably mounted within groove 410, and may be provided with teeth to engage gear teeth 454 of face gear 452, thereby rotating portion 450 as the head of the rotating member rotates.

Blade 500 may be coupled to the curved portion 310 of arm 300. In some embodiments, blade 500 may be a hemispherical blade curved on two axes. In other embodiments, blade 500 may have a curvature on only the vertical axis. However, any blade configuration that allows device 100 to function as described herein can be contemplated and provided as desired. Blade 500 may include a pair of pins 502 which may be slidably received within slit 314 of curved portion 310. Furthermore, in some embodiments, blades having alternate geometry may be used so as to negotiate around obstacles on the back side or rim of the acetabular cup. In yet further embodiments, a sheath (not shown) may be provided for the blade so as to protect surrounding soft tissue as well as the operator.

Connected between pin 460 and one or both of pins 502 may be a flexible connector (not shown). As rotating portion 450 is rotated by the head of the rotating shaft, the flexible connector can slidably oscillate blade 500 within slit 314. This allows blade 500 to be advanced, thereby allowing the blade to fully reach the apex of the cut being made by the blade oscillating to that point, such that a full cut is made along the hemisphere of the acetabular cup. Furthermore, oscillator assembly 400 may be slidably moved as desired within slit 312.

FIG. 7 shows an exemplary embodiment of a method 600 of operating an acetabular cup removal device 100 to remove an acetabular cup. In a preliminary step, the hip may be exposed by any known surgical technique. If the femur is also to be revised, then that component is may also be removed first. The acetabular liner, and any screws fixing the acetabulum may then be removed by any known technique. Subsequently, in a first step 602, a mounting ring 102 may be selected so as to match the particular size, type, brand, and/or model of the acetabular cup. Mounting ring 102 is then mounted, in step 604, to the acetabular cup by insertion of a fastening member, such as a screw, through fastening bore 122 and the acetabular cup, specifically through a central point on the surface of the acetabular cup. In step 606, an arm 300 that likewise matches the particular size, type, brand, and/or model of the acetabular cup is selected. The arm 300 is then coupled, at step 608, to mounting ring

102, along with rotor 200 and rotating portion 400, which may be standard components that do not need to be matched to a particular acetabular cup. At step 610, a blade 500 is selected that likewise matches the particular size, type, brand, and/or model of the acetabular cup, and slidably mounted within slit 314. Blade 500 is connected to rotating portion 400 by the connector extending therebetween.

The removal operation may now be commenced. At step 612, arm 300 may be rotated, up to 90 degrees with respect to the plane of ring 102, to an initial location such that the tip of the blade contacts the bone at the rim of the acetabular cup. The rotating member may then be powered so as to rotate rotating portion 450, which, via the flexible connector, causes the blade to oscillate about the longitudinal axis of bore 304, and advances the arm until the face of the acetabular cup is reached, at step 614. After the blade reaches the face of the acetabular cup, the rotating member may be powered down, the blade may be withdrawn from the resultant cut until the blade is at the rim of the acetabular cup, and arm 300 may be rotated about the longitudinal axis of bore 210, to a next adjacent location, at step 616.

In some embodiments, depending on the particular acetabular cup (for example, for cups without spikes thereon), the blade and arm may simply be rotated to the next adjacent location at step 616 without fully withdrawing the blade from the resultant cut. In embodiments, for example for cups having spikes, an alternatively shaped blade may be provided. Thus, at step 616 the base of the arrowhead of the blade may be driven past the spike and then the blade may be rotated about the longitudinal axis of bore 210 so as to remove the bone between the spike and the apex of the cup; the arm may then be rotated back to allow for withdrawal of the arrowhead of the blade and then rotated to the next adjacent location.

Steps 614-616 are then repeated such that the blade passes through the full 360° circumference of the acetabular cup. Once the full circumference is cut, the acetabular cup may be detached from the patient, and device 100 may subsequently be detached from the acetabular cup, at step 618.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An acetabular cup removal device, comprising:
   a mounting ring attachable to an acetabular cup;
   a rotor rotatably coupled to the mounting ring and rotatable about a first axis;
   an arm pivotably coupled to the rotor and pivotable about a second axis orthogonal to the first axis;
   an oscillator assembly configured to be coupled to the arm; and
   a blade configured to be coupled to the arm;
   wherein a rotating motion of a rotating portion of the oscillator assembly causes an oscillating motion of the blade.

2. The acetabular cup removal device of claim 1, wherein the oscillator assembly further comprises a tab extending vertically downward from the lower surface of the main block of the oscillator assembly which is slidably coupled to the arm.

3. The acetabular cup removal device of claim 1, wherein the blade is attached to the arm by pins, and the pins are slidably received by the arm.

4. The acetabular removal device of claim 1, wherein the blade has a shape that corresponds to a configuration of an acetabular cup.

5. An acetabular cup removal device, comprising:

a mounting ring attachable to an acetabular cup;

a rotor rotatably coupled to the mounting ring and rotatable about a first axis;

an arm pivotably coupled to the rotor and pivotable about a second axis orthogonal to the first axis;

an assembly configured to be coupled to the arm; and a blade configured to be coupled to the arm;

wherein a rotating motion of a rotating portion of the assembly causes a motion of the blade.

* * * * *